(12) United States Patent
Chiasson et al.

(10) Patent No.: US 11,654,128 B2
(45) Date of Patent: May 23, 2023

(54) METHODS AND COMPOSITIONS FOR TREATING ECTOPARASITE INFESTATIONS

(71) Applicant: Nuvo Pharmaceuticals (Ireland) Designated Activity Company, Dublin (IE)

(72) Inventors: Bernard Joseph Chiasson, Campbellville (CA); Robert Patrick Pearce, St-Laurent (CA); Chantal Paré, Saint-Hubert (CA)

(73) Assignee: Nuvo Pharmaceuticals (Ireland) Designated Activity Company, Dublin (IE)

( * ) Notice: Subject to any disclaimer, the term of this patent is extended or adjusted under 35 U.S.C. 154(b) by 0 days.

(21) Appl. No.: 17/743,201

(22) Filed: May 12, 2022

(65) Prior Publication Data

US 2022/0362198 A1    Nov. 17, 2022

Related U.S. Application Data

(60) Provisional application No. 63/188,274, filed on May 13, 2021.

(51) Int. Cl.
    *A61K 31/23*   (2006.01)
    *A61P 33/14*   (2006.01)
    *A61K 31/80*   (2006.01)

(52) U.S. Cl.
    CPC .............. *A61K 31/23* (2013.01); *A61K 31/80* (2013.01); *A61P 33/14* (2018.01)

(58) Field of Classification Search
    CPC .......... A61K 31/23; A61K 31/80; A61P 33/14
    See application file for complete search history.

(56) References Cited

U.S. PATENT DOCUMENTS

| 10,334,853 B2 | 7/2019 | van Buskirk et al. |
| 2018/0070593 A1* | 3/2018 | van Buskirk .......... A61K 31/80 |

FOREIGN PATENT DOCUMENTS

| CA | 2484183 | 6/2011 |
| EP | 1993363 B1 | 7/2010 |
| EP | 1499184 B1 | 9/2012 |
| JP | 2019031458 | 2/2019 |
| JP | 2019189533 | 10/2019 |
| WO | 2007104345 | 9/2007 |
| WO | 2012176131 | 12/2012 |
| WO | 2015162395 | 10/2015 |
| WO | 2017184537 | 10/2017 |

OTHER PUBLICATIONS

International Application No. PCT/IB2022/054491, International Search Report and Written Opinion dated Jul. 27, 2022.
Canadian Application No. CA 3,161,004, Office Action dated Jul. 22, 2022, 4 pages.
European Application No. EP22173252.2, Extended European Search Report dated Sep. 27, 2022, 7 pages.

* cited by examiner

*Primary Examiner* — Savitha M Rao
(74) *Attorney, Agent, or Firm* — Kilpatrick Townsend & Stockton LLP

(57) ABSTRACT

The present application includes compositions for treating ectoparasite infestations, including killing ectoparasites and/or their ova, the compositions comprising one or more fatty acid esters and one or more linear polymeric siloxanes. Also included are kits comprising the compositions and methods of treating ectoparasite infestations, including methods of killing ectoparasites and/or their ova, using the compositions.

30 Claims, No Drawings

METHODS AND COMPOSITIONS FOR TREATING ECTOPARASITE INFESTATIONS

CROSS-REFERENCE TO RELATED APPLICATIONS

The present application claims the benefit of priority from U.S. patent application No. 63/188,274, filed May 13, 2021, the contents of which are incorporated herein by reference in their entirety.

FIELD

The present application relates to compositions and methods thereof for killing ectoparasites including lice and/or their ova.

Introduction

Head lice infestation is a persistent problem with as many as 6-12 million people worldwide affected each year. The problem is particularly prevalent in preschool and elementary-age children aged 3-10 and their families. Head lice infestation is produced by the common head louse *Pediculus humanus capitis*, and typically causes itching of the scalp. As the lice feed on human blood, they may cause lesions to develop on the scalp, swollen glands on the neck or under arms, or other symptoms. Head lice infestation causes serious problems due to the related health concerns and the negative social implications of the infestation. Body lice are also bothersome to humans and carry the additional hazard of being the vectors of certain diseases, such as exanthematic or epidemic typhus and recurrent fever.

Various compositions are available for treating ectoparasite, including head lice infestations, which generally take a topical approach to treatment. Most of these treatments involve the use of insecticides that are harsh agents, thus raising toxicity concerns. The lice can also become resistant to the insecticides used and therefore the compositions can lose their effectiveness over time. Further, ova or eggs (the terms being interchangeable) of ectoparasites are often encased in protective sheaths which protect them from many toxic agents.

European patent no. EP1499184B1 describes compositions for treating ectoparasite infestations comprising a fatty acid ester in an amount sufficient for killing lice and a siloxane that is a volatile, non-polymeric cyclic siloxane.

European patent no. EP1993363B1 describes compositions for killing ectoparasites and/or their ova comprising a combination of a low viscosity linear polysiloxane, a high viscosity linear polysiloxane and a spreading agent. Exemplary compositions disclosed in EP 1993363 comprise greater than 90% of the linear polysiloxanes and less than 10% of the spreading agent. The high viscosity linear polysiloxane exemplified in this patent had a viscosity of 100 cSt. Further, the low viscosity linear polysiloxane exemplified in this patent had a viscosity of 1 cSt and such siloxanes are potentially environmentally toxic. In addition, the compositions of EP1993363B1 demonstrated low (e.g. 39.5%) ovicidal efficacy following a 45-minute application period.

There exists therefore a need for compositions for treating ectoparasite infestations without the use of harsh insecticides, and that are effective for the killing of ectoparasites and/or their ova.

SUMMARY

It has been shown herein that compositions comprising linear polymeric siloxanes such as polydimethylsiloxane having a low viscosity at 25° C., and a fatty acid ester such as isopropyl myristate are effective in killing ectoparasites including head lice and their ova. It has also been shown that in addition to adult ectoparasites, the compositions of the present application are effective at killing lice ova or louse eggs at different stages of development including at an early, undeveloped or undifferentiated egg stage (undeveloped nits), developed or differentiated egg stage (developed nits), and emergent or half-hatched egg stage.

The present application includes a composition comprising:
one or more fatty acid esters; and
one or more linear polymeric siloxanes.

The present application includes a kit comprising one or more compositions of the present application, and optionally instructions for use.

The present application includes a method for treating an ectoparasite infestation on a subject in need thereof comprising topically administering one or more compositions of the present application to the subject.

The present application also includes a use of one or more compositions of the application for the topical treatment of an ectoparasite infection on a subject. The present application also includes a use of one or more compositions of the application in the manufacture of a medicament for the topical treatment of an ectoparasite infection on a subject.

Other features and advantages of the present application will become apparent from the following detailed description. It should be understood, however, that the detailed description and the specific examples, while indicating embodiments of the present application, are given by way of illustration only and the scope of the claims should not be limited by these embodiments, but should be given the broadest interpretation consistent with the description as a whole.

DESCRIPTION OF VARIOUS EMBODIMENTS

I. Definitions

Unless otherwise indicated, the definitions and embodiments described in this and other sections are intended to be applicable to all embodiments and aspects of the present application herein described for which they are suitable as would be understood by a person skilled in the art.

As used in the present application, the singular forms "a", "an" and "the" include plural references unless the content clearly dictates otherwise. For example, an embodiment including "a siloxane" should be understood to present certain aspects with one siloxane, or two or more additional siloxanes.

The terms "about", "substantially" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies or unless the context suggests otherwise to a person skilled in the art.

In embodiments comprising an "additional" or "second" component, such as an additional or second siloxane, the second component as used herein is, different, for example chemically different, from the other components or first component. A "third" component is different from the other, first, and second components, and further enumerated or "additional" components are similarly different. Likewise, in the term "one or more" the "more" or additional components are different from the "one" component.

The term "administered" as used herein means administration of an effective amount or a therapeutically effective amount of one or more compositions of the present application to a subject.

The term "alkyl" as used herein, whether it is used alone or as part of another group, means straight or branched chain, saturated alkyl groups. The number of carbon atoms that are possible in the referenced alkyl group are indicated by the prefix "$C_{n1-n2}$". For example, the term $C_{1-10}$alkyl means an alkyl group having 1, 2, 3, 4, 5, 6, 7, 8, 9 or 10 carbon atoms.

The term "and/or" as used herein means that the listed items are present, or used, individually or in combination. In effect, this term means that "at least one of" or "one or more" of the listed items is used or present. The term "and/or" with respect to pharmaceutically acceptable salts and/or solvates thereof means that the compounds of the present application exist as individual salts and hydrates, as well as a combination of, for example, a solvate of a salt of a compound of the present application.

The term "composition(s) of the present application" and the like as used herein refers to a composition comprising a fatty acid ester and a linear polymeric siloxane.

As used in this application and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "consisting" and its derivatives as used herein are intended to be closed terms that specify the presence of the stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

As used herein, the term "effective amount" or "therapeutically effective amount" means an amount of one or more compositions of the present application that is effective, at dosages and for periods of time necessary to achieve the desired result.

The term "ectoparasite" as used herein refers to any organism of the phylum Arthropoda that lives on a host, from which they derive their sustenance. The ectoparasite may be an animal or a plant ectoparasite.

The term "infestation" as used herein refers to the presence of live ectoparasites on a subject, including eggs and/or larvae thereof.

The term "fatty acid ester" as used herein refers to any acid derived from fats by hydrolysis and having from 6 to 22 carbon atoms. An ester is a functional derivative of a carboxylic acid, where the —OH group of the carboxylic acid has been replaced by an —OR, OR being an alkoxy group.

The terms "kill" or "killing" as used herein means causing the death of live lice and/or causing the death of or preventing the development/hatching of larvae or ova thereof.

The term "nit comb" as used herein refers to a comb for ordering hair and thereby removing ectoparasite nits (eggs) by passing the comb through the hair.

The term "pharmaceutically acceptable" means compatible with the treatment of subjects.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to a subject.

The term "polymeric" as used herein means having repeating monomeric units. The monomeric units may be the same or different monomeric units.

The term "rinse-off composition" as used herein refers to a composition suitable for being used on, administered, or applied topically to a subject and subsequently removed by rinsing with a liquid such as water. The term "rinse-off" may be used interchangeably with "wash-off".

The term "rinse" or "rinsing" as used herein means to substantially remove or wash a composition from or off a subject using a liquid such as water. The term "substantially" in this context means that all or almost all of the composition is removed, i.e., less than 20%, 10%, 5%, 4%, 3%, 2%, 1%, 0.5%, or 0.1% of the composition remains on the subject.

The term "siloxane" as used herein refers to a compound having the Si—O—Si bond, the main chemical bond found in silica.

The term "subject" as used herein includes all members of the animal and plant kingdom including mammals, and suitably refers to humans.

The term "treating" or "treatment" as used herein and as is well understood in the art, means an approach for obtaining beneficial or desired results, including clinical results. Beneficial or desired results include, but are not limited to alleviation or amelioration of one or more symptoms or conditions, diminishment of extent of one or more symptoms or conditions, stabilized (i.e. not worsening) state of one or more symptoms or conditions, preventing spread of one or more symptoms or conditions, diminishment of the reoccurrence of one or more symptoms or conditions (whether partial or total), whether detectable or undetectable. "Treating" and "treatment" as used herein also include prophylactic treatment. Treatment methods comprise administering to a subject an effective amount of one or more of the compositions of the present application and optionally consist of a single administration, or alternatively comprise a series of administrations.

The viscosity units expressed herein refer to the viscosity of a material at 25° C. as determined using, for example, a Brookfield viscometer according to ASTM D4287.

II. Compositions and Kits of the Application

Disclosed herein are compositions that kill ectoparasites, including, advantageously, their ova. Unlike comparator compositions, in some embodiments, all ova from head lice were killed at the undeveloped stages which indicates that the ova were killed early on in development.

For example, the composition of the present application can be a pharmaceutical composition. For example, the composition of the present application can be a device.

The present application therefore includes a composition comprising:
one or more fatty acid esters; and
one or more linear polymeric siloxanes.

In some embodiments, the composition comprises greater than 10 wt % of the one or more fatty acid esters by total weight of the composition. In some embodiments, the composition comprises less than 65 wt % of the one or more linear polymeric siloxanes by total weight of the composition. In some embodiments, the composition comprises one linear polymeric siloxane. In some embodiments, the one linear polymeric siloxane is of a specific viscosity at 25° C.

In some embodiments, the composition is free of pesticides. It can be appreciated that although the composition of the present application is effective at killing ectoparasites and is thus pesticidal, when the composition of the present application is said to be free of pesticides, it is intended to mean that the composition is free of traditional and/or toxic pesticidal chemicals. For example, such pesticides can include Piperonyl butoxide; Permethrin, ivermectin, malathion, Spinosad, lidane, Methoprene.

In some embodiments, the composition kills greater than 79%, 80%, 85%, 90%, 95% or 99% of ectoparasites and ova in about 12 hr, about 18 hr or about 24 hr following about 5 to about 10 minutes of topical contact of the composition with a subject. In some embodiments, the topical contact is for about 9 to about 11 minutes. In some embodiments, the contact is for about 10 minutes. In some embodiments, the contact is for about 5 minutes. In some embodiments, the contact is for less than 5 minutes. In some embodiments, the contact is for less than 45 minutes. In some embodiments, the ectoparasites and ova are head lice and their ova or nits. In some embodiments, the composition kills greater than 79%, 80%, 85%, 90%, 95%, or 99% is achieved using multiple applications of the composition, for example, twice for about 5 to about 10 minutes during a 7- to 10-day period. In some embodiments, the composition kills greater than 79%, 80%, 85%, 90%, 95% or 99% of ectoparasites and ova from a single contact of the composition for about 5 to about 10 minutes. In some embodiments, the composition has a faster onset of action than a comparator formulation, wherein the comparator formulation contains 40-42 wt % Dimethicone 1 cSt, 50% Dimethicone 100 cSt and 5 wt % medium chain triglycerides. In some embodiments, the contact of the comparator formulation is for at least 45 minutes.

In some embodiments, the one or more fatty acid esters are selected from alkyl esters of fatty acids. The one or more fatty acids can be saturated aliphatic fatty acids, or unsaturated fatty acids. In some embodiments, the one or more fatty acid esters are selected from myristate, laurate, palmitate, stearate, arachidate, behenate, lignocerate, palmitoleate, oleate, linoleate, linolenate, and arachidonate. In some embodiments, the one or more alkyl esters are selected from isopropyl esters, methyl esters, ethyl esters, and propyl esters. In some embodiments the composition comprises one fatty acid ester. In some embodiments, the fatty acid ester is isopropyl myristate.

In some embodiments, the linear polymeric siloxane is characterized by viscosity at 25° C. Alternatively or additionally, the linear polymeric siloxane is characterized by average molecular weight, number averaged molecular weight (Mn), Z averaged molecular weight (Mz), and/or a Z+1 average molecular weight (Mz+1). The average in each case is calculated from a distribution of different chain lengths in the linear polymeric siloxane. It can be appreciated that linear polymeric siloxanes often exist as a mixture of siloxane polymers of different chain lengths due to the nature of polymerization reactions. As such, it can be appreciated that a linear polymeric siloxane as referred to herein can comprise a distribution of chain lengths, and thus a distribution of molecular weights.

In some embodiments, the one or more linear polymeric siloxanes are non-volatile.

In some embodiments, the one or more linear polymeric siloxanes are linear polydialkylsiloxanes. In some embodiments, the one or more linear polymeric siloxanes are polydimethylsiloxanes.

In some embodiments, the one or more linear polymeric siloxanes have a low viscosity. In some embodiments, the one or more linear polymeric siloxanes have a viscosity at 25° C. of less than 90 cSt. In some embodiments, the one or more linear polymeric siloxanes have a viscosity at 25° C. of less than 80 cSt, less than 70 cSt, less than 60 cSt, or less than 55 cSt.

In some embodiments, the one or more linear polymeric siloxanes have a viscosity at 25° C. of more than 1 cSt. In some embodiments, the one or more linear polymeric siloxanes have a viscosity at 25° C. of at least 5 cSt or about 5 cSt. In some embodiments, the one or more linear polymeric siloxanes have a viscosity at 25° C. of at least 10 cSt or about 10 cSt. In some embodiments, the one or more linear polymeric siloxanes have a viscosity at 25° C. of at least 50 cSt or about 50 cSt. In some embodiments, the composition does not contain linear siloxanes that are 1 cSt. In some embodiments, the composition does not contain linear siloxanes that are 100 cSt. In some embodiments, the composition does not contain linear siloxanes that are 1 cSt or 100 cSt. In some embodiments, the composition does not contain linear siloxanes that are <10 cSt. In some embodiments, the composition does not contain linear siloxanes that are >90 cSt. In some embodiments, the composition does not contain linear siloxanes that are <10 cSt or >90 cSt.

In some embodiments, the one or more linear polymeric siloxanes have a viscosity at 25° C. of greater than 1 cSt to less than 90 cSt. In some embodiments, the one or more linear polymeric siloxanes have a viscosity at 25° C. of about 2 cSt to about 89 cSt. In some embodiments, the one or more linear polymeric siloxanes have a viscosity at 25° C. of about 2 cSt to about 60 cSt. In some embodiments, the one or more linear polymeric siloxanes have a viscosity at 25° C. of about 10 cSt to about 50 cSt. In some embodiments, the one or more linear polymeric siloxanes have a viscosity at 25° C. of about 3 cSt to about 50 cSt. In some embodiments, the one or more linear polymeric siloxanes have a viscosity at 25° C. of about 3 cSt to about 15 cSt. In some embodiments, the compositions are free of linear siloxanes that have a viscosity at 25° C. of less than 10 cSt. In some embodiments, the compositions are free of linear siloxanes that have a viscosity at 25° C. of 90 cSt or more.

In some embodiments, the one or more linear polymeric siloxanes each has an average molecular weight (MW) of about 900 g/mol to about 6200 g/mol. In some embodiments, the one or more linear polymeric siloxanes each has an average MW of about 900 g/mol to about 4000 g/mol, about 1000 g/mol to about 3000 g/mol, or about 1040 g/mol to about 2500 g/mol. In some embodiments, the one or more linear polymeric siloxanes each has an average MW of about 1400 g/mol to about 1800 g/mol, or about 1500 g/mol to about 1700 g/mol. In some embodiments, the one or more linear polymeric siloxanes each has an average MW of about 5500 g/mol to about 6200 g/mol, or about 5700 g/mol to about 6100 g/mol.

In some embodiments, the one or more linear polymeric siloxanes each has a number averaged molecular weight (Mn) of about 800 g/mol to about 4700 g/mol. In some embodiments, the one or more linear polymeric siloxanes each has a Mn of about 1000 g/mol to about 4500 g/mol, or about 1100 g/mol to about 4300 g/mol. In some embodiments, the one or more linear polymeric siloxanes each has a Mn of about 1100 g/mol to about 1600 g/mol, or about 1200 g/mol to about 1500 g/mol. In some embodiments, the one or more linear polymeric siloxanes each has a Mn of about 4000 g/mol to about 4500 g/mol, or about 4050 g/mol to about 4300 g/mol.

In some embodiments, the one or more linear polymeric siloxanes each has a Z averaged molecular weight (Mz) of about 1500 g/mol to about 9500 g/mol. In some embodiments, the one or more linear polymeric siloxanes each has a Mz of about 1700 g/mol to about 9000 g/mol, or about 1900 g/mol to about 8500 g/mol. In some embodiments, the one or more linear polymeric siloxanes each has a Mz of about 1800 g/mol to about 2700 g/mol, or about 1900 g/mol to about 2200 g/mol. In some embodiments, the one or more linear polymeric siloxanes each has a Mz of about 7500 g/mol to about 8700 g/mol, or about 8000 g/mol to about 8600 g/mol.

In some embodiments, the one or more linear polymeric siloxanes each has a Z+1 average molecular weight (Mz+1) of about 1700 g/mol to about 14500 g/mol. In some embodiments, the one or more linear polymeric siloxanes each has a Mz+1 of about 2000 g/mol to about 13000 g/mol, or about 2200 g/mol to about 12500 g/mol. In some embodiments, the one or more linear polymeric siloxanes each has a Mz+1 of about 2100 g/mol to about 3000 g/mol, or about 2200 g/mol to about 2900 g/mol. In some embodiments, the one or more linear polymeric siloxanes have a Mz+1 of about 9000 g/mol to about 13500 g/mol, or about 10000 g/mol to about 12500 g/mol.

In some embodiments, the composition comprises one linear polymeric siloxane. In some embodiments, the composition comprises one linear polymeric siloxane and one or more fatty acid esters. In some embodiments, the composition comprises one linear polymeric siloxane and one fatty acid ester. In some embodiments, the composition comprises more than one linear polymeric siloxane and one fatty acid ester. In some embodiments, the composition comprises more than one linear polymeric siloxane and more than one fatty acid ester.

In some embodiments, the composition comprises greater than 10 wt % of the one or more fatty acid esters by total weight of the composition. In some embodiments, the composition comprises greater than 20 wt % of the one or more fatty acid esters by total weight of the composition. In some embodiments, the composition comprises greater than 30 wt % of the one or more fatty acid esters by total weight of the composition. In some embodiments, the composition comprises greater than 40 wt % of the one or more fatty acid esters by total weight of the composition. In some embodiments, the composition comprises about 25 wt % of the one or more fatty acid esters. In some embodiments, the composition comprises less than 65 wt % of the one or more linear polymeric siloxanes by total weight of the composition. In some embodiments, the composition comprises less than 60 wt % of the one or more linear polymeric siloxanes by total weight of the composition. In some embodiments, the composition comprises less than 55 wt % of the one or more linear polymeric siloxanes by total weight of the composition. In some embodiments, the composition comprises about 25 wt % to about 75 wt % of the one or more fatty acid esters and about 25 wt % to about 75 wt % of the one or more linear polymeric siloxanes, by total weight of the composition. In some embodiments, the composition comprises about 35 wt % to about 65 wt % of the one or more fatty acid esters and about 35 wt % to about 65 wt % of the one or more linear polymeric siloxanes, by total weight of the composition. In some embodiments, the composition comprises about 40 wt % to about 60 wt % of the one or more fatty acid esters and about 40 wt % to about 60 wt % of the one or more linear polymeric siloxanes, by total weight of the composition. In some embodiments, the composition comprises about 25 wt % of the one or more linear polymeric siloxanes. In some embodiments, the composition comprises about 50 wt % of the one or more fatty acid esters and about 50 wt % of the one or more linear polymeric siloxanes, by total weight of the composition. In some embodiments, the composition comprises about 25 wt % of the one or more fatty acid esters and about 25 wt % of the one or more linear polymeric siloxanes, by total weight of the composition. In some embodiments, the weight ratio of the one or more fatty acid esters to the one or more linear polymeric siloxanes is about 2:1 to about 1:2. In some embodiments, the ratio of the one or more fatty acid esters to the one or more linear polymeric siloxanes is about 1:1.

In some embodiments, the composition of the present application consists of or consists essentially of the one or more fatty acid esters and the one or more linear polymeric siloxanes.

In some embodiments, the composition further comprises one or more additives selected from excipients, carriers, diluents, and combinations thereof. In some embodiments, the excipients, carriers, diluents, and combinations thereof are selected from water, oil (e.g. mineral oil), and the like. In some embodiments, the compositions of the present application comprise cosmetic agents, such as fragrances and/or skin care agents that are known to be used in topical compositions for treating ectoparasite infestations.

In some embodiments, the compositions of the present application are formulated into pharmaceutical compositions or devices for topical administration to a subject. In some embodiments, the topical administration includes administration to a surface of the subject. In some embodiments, the topical administration includes administration to the scalp, skin, fur and/or hair of the subject. In some embodiments, the composition is for external application in the treatment of ectoparasitic infestations.

In some embodiments, the compositions of the present application are spreadable. In some embodiments, the compositions of the present application are fast drying. In some embodiments, the compositions of the present application have low mammalian toxicity. In some embodiments, the compositions of the present application are hair/fur and skin compatible. In some embodiments, the compositions of the present application are substantially odourless.

In some embodiments, the compositions of the present application are substantially free of alcohol, such as aliphatic alcohols.

In some embodiments, the compositions of the present application are for use in the topical treatment of an ectoparasite infestation. In some embodiments, the ectoparasite infestation is an infestation of ectoparasites selected from head lice, body lice (e.g., *Pediculus humanus*), crab lice (e.g., *Phthirus pubis*), mites (scabies), fleas and ticks, including ova and/or larvae thereof. In some embodiments, the ectoparasites are head lice. In some embodiments, the ova of the head lice are undeveloped nits, developed nits, half-hatched ova, or combinations thereof.

In some embodiments, the compositions of the present application are formulated into personal care products. For example, the personal care products can be a rinse-off composition (e.g. shampoo and/or a foaming product). In some embodiments, the rinse-off composition is administered or used by topical application to the body, for example, on the skin, scalp, hair, and/or another anatomical surface. The body is either wet or dry when the rinse-off composition is administered or used. Optionally, the body is wetted with water prior to the administration or use of the composition. Optionally, the rinse-off composition is lathered using water after administration or use, and before or during being removed by rinsing (e.g., being rinsed off). In some embodiment, the removing by rinsing removes a substantial amount of the rinse-off composition.

In some embodiments, the rinse-off composition is selected from a cleansing composition, a conditioning composition, a moisturizing composition, and a foaming composition, and combinations thereof. In some embodiments, the cleansing composition includes, but not is not limited to body cleansers or washes, and bath and shower products such as washes, foams, and gels. In some embodiments, the hair care composition is a shampoo composition and/or hair conditioning composition. In some embodiments, the foam composition is a gel, and/or mousse foam. In some embodiments, the rinse off-composition, further comprises one or more of foaming agents. In some embodiments the foaming agent is a surfactant. In some embodiments the surfactant is a non-ionic surfactant. Non-limiting examples of non-ionic surfactants include Brij™ O10, Brij 35, Brij 98, Tween™ 20, Tween 60 and Tween 80. In some embodiments, the composition comprises about 0.5 to about 20% wt of the surfactant. In some embodiments, the composition comprises about 1, 2, 3, 4, 5, 6, 7, 8, 9, 10, 11, 12, 13, 14 or 15% wt of the surfactant. In some embodiments, the composition may include fragrances such as mint flavour.

The present application also includes kits comprising the compositions of the application. Therefore, the present application includes a kit comprising:

one or more compositions comprising
one or more fatty acid esters; and
one or more linear polymeric siloxanes; and
optionally, instructions for use.

In some embodiments, the one or more compositions comprise greater than 10 wt % of the one or more fatty acid esters by total weight of the composition. In other embodiments, the one or more compositions comprise less than 65 wt % of the one or more linear polymeric siloxanes, by total weight of the composition. In further embodiments, the one or more compositions comprise one linear polymeric siloxane. In some embodiments, the one linear polymeric siloxane is of a specific viscosity at 25° C. as described herein.

In some embodiments, the kit further comprises a nit comb. It is appreciated that although a nit comb is not necessary for the effectiveness of the compositions of the present application, a nit comb can facilitate removal of ectoparasites and ova thereof from the hair/fur of the subject. Examples of suitable nit combs include but are not limited to the LICEMEISTER® (National Pediculosis Association, Inc., Newton, Mass.), ACU-MED® Lice Comb (Health Enterprises, N. Attleboro, Mass.), and MEDI-SWEEP Lice Comb (Classic Products, Oxnard, Calif.).

The kits of the present application can be in a package. For example, the package can be a box, and/or a wrapping that surrounds the kit. In some embodiments, the nit comb is provided inside the package. In other embodiments, the nit comb is attached to the outside of the package. In some embodiments, the kit does not include a comb. In some embodiments, the comb may be sold separately from the kit.

In some embodiments, the kits of the present application further comprise a marker such as a fluorescent dye. In some embodiments, the kits of the present application further comprise a shower cap.

In some embodiments, the package includes instructions. In some embodiments, the instructions advise to apply the composition to the hair and scalp. In some embodiments, the instructions advise that the hair and scalp must be fully wetted with the composition. In some embodiments, the instructions indicate how long to apply the composition to the hair and scalp (e.g. about 5 to about 10 minutes of contact). In some embodiments, the instructions indicate the application period (e.g. once or twice in a period of 7 to 10 days).

III. Methods and Uses of the Present Application

In another aspect, the present application includes a method for treating an ectoparasite infestation on a subject in need thereof comprising topically administering one or more compositions of the present application to the subject.

The present application also includes a use of one or more compositions of the application for the topical treatment of an ectoparasite infection on a subject. The present application also includes a use of one or more compositions of the application in the manufacture of a medicament for the topical treatment of an ectoparasite infection on a subject.

The one or more compositions of the application are as defined in Section II above.

For example, the administration is topical administration. By a topical administration, it is meant that the composition is applied to the exterior of the treated subject, e.g. to the exterior skin, hair, or fur. This application includes, but is not limited to, manual application or application by various automated means, for example, pouring, spraying, shampooing or painting onto a treated subject, or other means. For example, the topical administration is to the skin including scalp of the subject. In some embodiments, topical administration does not include penetration of the composition to the interior of the treated subject, e.g. the composition does not substantially penetrate the skin of the treated subject. As another example, administration of the composition of the invention is as a device.

In some embodiments, in the context of treating an ectoparasite infestation, or killing ectoparasites, the one or more compositions are administered in an amount, for example an effective amount, that for example decreases the number of live, developing and/or replicating ectoparasites and/or larvae or ova thereof compared to the number of live, developing and/or replicating ectoparasites and/or larvae or ova thereof without administration of one or more compositions of the present application.

In some embodiments, the treating or treatment comprises killing the ectoparasites causing the ectoparasite infestation. In some embodiments, the treating or treatment comprises killing ova of the ectoparasites causing the ectoparasite infestation. In some embodiments, the treating or treatment comprises killing the ectoparasites causing the ectoparasite infestation and killing ova of the ectoparasites causing the ectoparasite infestation. In some embodiments the treating or treatment comprises killing ova of the ectoparasites that are at any developmental stage. In some embodiments, the treating or treatment comprises killing ova of the ectoparasites that are undeveloped ova, developed ova, half-hatched ova, or combinations thereof.

In some embodiments, the composition kills greater than 79%, 80%, 85%, 90%, 95% or 99% of ectoparasites and/or their ova in about 12 hr, about 18 hr or about 24 hr following about 5 to about 10 minutes of topical contact of the composition to a subject. In some embodiments, the topical contact is for about 9 to about 11 minutes. In some embodiments, the contact is for about 10 minutes. In some embodiments, the composition kills at least 5%, 10%, 15%, 20% or 25% more ectoparasite ova than a comparator composition. In some embodiments, the comparator composition comprises 50 wt % isopropyl myristate and 50 wt % cyclomethicone. In some embodiments, the composition kills greater than 79%, 80%, 85%, 90%, 95% or 99% of ectoparasite ova in about 12 hr, about 18 hr or about 24 hr following about 5 to about 10 minutes of topical contact of the composition to a subject regardless of the stage of development of the ectoparasite ova. In some embodiments, the ectoparasite ova are head lice ova, or nits. In some embodiments, the ectoparasites ova are at an early, undeveloped or undifferentiated egg stage (undeveloped nits), developed or differentiated egg stage (developed nits), emergent or half-hatched egg stage or a mixture thereof.

In some embodiments, the composition kills at least 5%, 10%, 15%, 20%, 25% or 30% more ectoparasite ova following contact for about 5 to about 10 minutes than a comparator composition that is applied for 45 minutes. In some embodiments, the comparator formulation comprises 40-42 wt % Dimethicone 1 cSt, 50% Dimethicone 100 cSt and 5 wt % medium chain triglycerides. In some embodiments, the composition has a faster onset of action than the comparator formulation. In some embodiments, the composition is less toxic than the comparator formulation. In some embodiments, the composition has fewer ingredients than the comparator formulation. In some embodiments, the composition comprises one linear siloxane (e.g. 50 cSt). In some embodiments, the composition comprises less than 65% wt of the one linear siloxane.

In some embodiments, the composition is a rinse-off composition. In some embodiments, the composition is substantially removed or washed from the subject after contacting the subject for a period of time as described herein. In some embodiments, the composition is rinsed off, wherein substantially all or all of the composition, and if applicable extraneous debris, is removed or washed off using a liquid such as water. The composition can also be removed by using wipes and/or clothes in the place of or in addition to the liquid. It can be appreciated that using wipes and/or clothes can be particularly helpful with soaps and other related products.

In some embodiments, the ectoparasite infestation is caused by ectoparasites selected from head lice, body lice (e.g., *Pediculus humanus*), crab lice (e.g., *Phthirus pubis*), mites (scabies), fleas and ticks, and ova and/or larvae thereof. In some embodiments, the ectoparasites are head lice. In some embodiments, the ova of the head lice are undeveloped ova, developed ova, half-hatched ova, or combinations thereof. In some embodiments, the ova of the head lice are undeveloped ova.

In some embodiments, the administering comprises contacting the one or more compositions with an area on the subject where the infestation is present. In some embodiments, the area is the skin or the scalp of the subject. In some embodiments, the area is any hair or fur on the subject. In some embodiments, the area is the skin or scalp of the subject and any hair or fur associated with the skin or scalp.

In some embodiments, contacting is for about 1 minute to up to several hours. In some embodiments, the contacting is for about 5 minutes to about 6 hours. In some embodiments, the contacting is for about 5 minutes to about 3 hours. In some embodiments, the contacting is for about 5 minutes to about 2 hours. In some embodiments, the contacting is for about 5 minutes to about 1 hour. In some embodiments, the contacting is for about 5 minutes to about 40 minutes. In some embodiments, contacting is for about 5 minutes to about 15 minutes. In some embodiments, the contacting is for about 9 to about 11 minutes. In some embodiments, the contacting is for about 10 minutes. In some embodiments, the contacting is for about 5 minutes. In some embodiments, the contacting is less than 5 minutes.

In some embodiments, the benefit of the composition over a comparator formulation includes a reduction in the application period required to treat the infestation, the comparator formulation comprising 40-42 wt % Dimethicone 1 cSt, 50% Dimethicone 100 cSt and 5 wt % medium chain triglycerides. An application or contact period of 45 minutes is significantly inconvenient, especially when applying the treatment to children. Shorter duration of contact, e.g. about 5 to about 10 minutes, is highly desirable. For rinse-off compositions, a shorter duration of contact of about 5 to about 10 minutes is also preferred. Contact periods greater than 10 minutes, e.g. 45 minutes for the comparator formulation, present a significant inconvenience to the user as the typical shower time in the United States based upon Environmental Protection Agency (EPA) estimates is about eight minutes.

In some embodiments, the one or more compositions of the application are administered or used in an amount of about 10 g to about 160 g. In some embodiments, the one or more compositions of the application are administered or used in an amount of about 25 g to about 140 g. In some embodiments, the one or more compositions of the application are administered or used in an amount of about 27 g to about 135 g. In some embodiments, the one or more compositions of the application are administered or used in an amount of about 10 mL to about 200 mL. In some embodiments, the one or more compositions of the application are administered or used in an amount of about 20 mL to about 175 mL. In some embodiments, the one or more compositions of the application are administered or used in an amount of about 30 mL to about 150 mL.

In some embodiments, the one or more compositions of the application are administered or used at least 1 time per day. In some embodiments, the one or more compositions of the application are administered or used at 1 time per day, 2 times per day, 3 times per day or 4 times per day. In some embodiments, the one or more compositions of the application are administered or used 1, 2, 3, 4, 5, 6, or 7 times per week. In some embodiments, the one or more compositions of the application are administered or used as a one-time use. In some embodiments, the one or more compositions of the application are administered or used twice. In some embodiments, the one or more compositions of the application are administered twice during a 7- to 10-day period. In some embodiments, the one or more compositions of the application are administered or used once or twice a month. In some embodiments, the one or more compositions of the application are administered or used once or twice a year. The length of the treatment period depends on a variety of factors, such as the severity of the infestation, the age of the subject, the concentration and/or the activity of the compositions of the present application, and/or a combination thereof. It will also be appreciated that the amount of the one or more compositions of the application administer or used for the treatment may increase or decrease over the course of a particular treatment regime. In some embodiments, the one or more compositions of the application are administered or used in an amount and for duration sufficient to treat the infestation, i.e. to remove or eliminate the ectoparasite infestation on the subject. In some embodiments, re-application of the composition is not required.

In an embodiment, the subject is a mammal. In another embodiment, the subject is human. In some embodiments, the subject in need thereof is any subject with or having an ectoparasite infestation.

In some embodiments, the subject is a household pet. Any mammalian pet may be treated using these methods (e.g., a dog or cat). In some embodiments, the compositions spread evenly and with little effort. In some embodiments, the compositions dry quickly. Thus, they may be conveniently used with great effectiveness and little or no discomfort to the treated animal. The methods and compositions may also be used to treat infestations of ectoparasites such as fleas and ticks on domestic animals such as bovines, equines, porcines, ovines, etc. The person of ordinary skill in the art will realize that animals are primarily subject to flea and tick infestations but that porcines and other domestic animals are also subject to tick and lice infestations (known as *Haematopinus* spp.), and that the present compositions will be effective for both.

In some embodiments, the compositions are applied by the subject. In some embodiments, the compositions are applied by someone other than the subject. In some embodiments, the compositions are applied to a subject by a parent, relative or teacher. In some embodiments, the compositions are applied to the subject at home, in a clinic or in a school setting. In some embodiments, the compositions are applied to the subject by a veterinarian, groomer or the like. In some embodiments, the compositions are applied by a haircare professional. In some embodiments, the compositions are applied by a healthcare professional such as a nurse, a doctor, a pharmacist, or a technician. In some embodiments, the compositions are applied by a homecare professional or a personal care professional.

In some embodiments, the subject is a plant or a crop. In some embodiments, the one or more compositions, methods and uses are particularly useful in the context of a greenhouse, where individual plants may be treated with one or more compositions of the application to destroy aphids, or other plant parasites such as, for example, white flies, spider mites, and other sucking insects. Other plants include high value or ornamental plants, where undamaged foliage is of particular importance, or plants that bear fruit that is more desirable if undamaged. Such damage is frequently a result of applying chemical insecticides or pediculocides, which dry on the foliage, or is the result of the plant parasite activity. The methods and uses of the application comprise topically applying one or more compositions of the application to the plant to be treated. In some embodiments, the compositions of the present application have no detrimental effect on the treated plant. In some embodiments, it is desirable to utilize one or more compositions of the application as a carrier with the addition of other active compounds for the treatment of plants. In some embodiments, the compositions of the present application may be useful as a carrier of fungicides, insecticides, or herbicides, because they possess the desirable properties of spreading easily and evenly, and does not "burn" or otherwise cause damage to the crops, foliage, or fruit. In some embodiments, the compositions dry quickly. Pesticides, specifically fungicides, herbicides, and insecticides that are not soluble in water can be applied advantageously using the one or more compositions of the application. For example, pyrethroids, organophosphates such as malathion and diazinon, pyrroles, or more generally azoles, glyphosate, nicotinoids, and triazines may be applied using one or more compositions of the present application.

In some embodiments, in the context of application to or use on livestock or domestic animals, the one or more compositions of the present application contain no solvents that are irritating to the treated animals. Permethrin, macrolides such as ivermectin, doramectin, moxidectin, abamectin, emamectin, eprinomectin, mycins such as milbemycin, and fungicides such as the azoles can be applied with one or more compositions of the present application as the carrier and spreader. The azoles can include the imidazoles and the triazoles. The imidazoles include, for example, clotrimazole, miconazole, ketoconazole, econazole, and sulconazole. The triazoles include, for example, itraconazole and fluconazole.

EXAMPLES

The following non-limiting examples are illustrative of the present application.

General Methods

Exemplary linear polymeric siloxanes used in the Examples below were purchased from Dow Corning™ (Dow Corning TI-1050 Fluid, 5 cSt, 10 cSt, and 50 cST CAS Number 63148-62-9). The properties of Dow Corning TI-1050 Fluid, 5 cSt, 10 cSt and 50 cST are presented in Table 1A.

TABLE 1A

| Property (Unit) | 5 cSt | 10 cSt | 50 cSt |
| --- | --- | --- | --- |
| Viscosity at 25° C. (cSt) | 4.5-5.5 | 9-11 | 47.5-52.5 |
| Appearance | Crystal clear, free of sediment or suspended matter | Crystal clear, free of sediment or suspended matter | Crystal clear, free from suspended matter |
| Flash point | <=250° F. | >=325° F. | >100° C. (Closed cup) |
| Refractive index | 1.3950-1.3990 | 1.3980-1.4000 | 1.4010-1.4030 |
| Specific gravity | 0.910-0.920 g/ml | 0.934-0.940 g/ml | 0.957-0.963 |
| Acid number | <=0.05 | <=0.01 mgK/g | <=0.01 mgK/g |

The exemplary linear polymeric siloxanes used in the examples below have been assessed by gel permeation chromatography (GPC). Their molecular distribution information is presented in Table 1B.

TABLE 1B

| Sample | Mn | Mw | Mz | Mz + 1 |
| --- | --- | --- | --- | --- |
| 10 cSt (lot 1) | 1,392 | 1,682 | 2,129 | 2,861 |
| 10 cSt (lot 2) | 1,402 | 1,661 | 2,007 | 2,441 |

TABLE 1B-continued

| Sample | Mn | Mw | Mz | Mz + 1 |
|---|---|---|---|---|
| 50 cSt (lot 1) | 4,204 | 5,856 | 8,379 | 12,273 |
| 50 cSt (lot 2) | 4,184 | 5,964 | 8,398 | 11,391 |
| 5 cSt (lot 1) | 921 | 1039 | 1199 | 1400 |
| 5 cSt (lot 2) | 923 | 1046 | 1218 | 1445 |

Isopropyl myristate was purchased from IOI Oleochemical in Malaysia.

Example 1 Preparation of Compositions of the Present Application

The compositions of the present application can be prepared using the general method described below.

An amount of the linear polymeric siloxane was combined with an amount of the fatty acid ester. The resulting mixture was stirred to optionally create a vortex to ensure thorough mixing. The mixture was stirred for about 15 minutes. Thorough mixing was assessed by taking a sample from the top, the middle and the bottom of the container containing the composition and determining the specific gravity of the samples. If the specific gravity of the three samples has an RSD of less than or equal to 3.5%, the compositions were determined to be thoroughly mixed.

Exemplary compositions Formulation 1 (F1) Formulation 2 (F2) and Formulation 3 (F3) of the present application were prepared using the general method as described above. The amounts and the identity of linear polymeric siloxane and fatty acid ester used, and the specific gravity of the compositions are shown in Tables 2 to 4.

TABLE 2

Compositions F1

| Component | F1 |
|---|---|
| TI-1050 5 cSt | 5.50 kg |
| Isopropyl myristate | 5.50 kg |
| Specific Gravity | 0.8851 g/ml (% RSD about 0.05%) |

TABLE 3

Compositions F2

| Component | F2 |
|---|---|
| TI-1050 10 cSt | 5.50 kg |
| Isopropyl myristate | 5.50 kg |
| Specific Gravity | 0.8941 g/ml (% RSD about 0.2%) |

TABLE 4

Compositions F3

| Component | F3 |
|---|---|
| TI-1050 50 cSt | 3.00 kg |
| Isopropyl myristate | 3.00 kg |
| Specific Gravity | 0.9054 g/ml (% RSD about 0.0%) |

Example 2 Activity Against Louse Aids

The activity of the exemplary compositions F1 and F2 against louse eggs was determined using ASTM test method E1517 13 (Standard Test Method for Determining Effectiveness of Liquid, Gel, Cream, or Shampoo Insecticide Against Human Louse Ova). A commercially available anti-lice composition containing 50 wt % isopropyl myristate and 50 wt % cyclomethicone was used as comparator (RComparator). Water was used as a negative control.

Insects Used in the Tests

Body louse eggs, *Pediculus humanus humanus*, were obtained from the laboratory culture maintained by an independent contract laboratory using rabbits as the source of maintenance feeding as per the ASTM E1517 13 test method.

Test Method

The eggs were tested according to the test method: ASTM E1517 13 method: Standard Test Method for Determining the Effectiveness of Liquid, Gel, Cream, or Shampoo Insecticides Against Human Louse Ova. The test procedure deviated from the provisions of the ASTM regarding the number of replicates using 3 instead of 5. All other methodology in the ASTM E1517 13 method was followed accordingly.

In summary, three replicates of 30 louse eggs were immersed in the test compositions for the incubation time indicated below. The louse eggs were then washed, rinsed with water and blotted dry, and incubated in separate petri dishes. For the negative control, the eggs were processed as with the eggs treated with the test compositions but immersed in water. When all the control eggs hatched (approximately 12 days), all replicates were examined to determine the state of the eggs.

Test Products

F1, 3 replicates, incubation time=10 minutes at 32° C.
F2, 3 replicates, incubation time=10 minutes at 32° C.
RComparator, 3 replicates, incubation time=10 minutes at 32° C.
Negative control, water, 3 replicates, incubation time=10 minutes at 32° C.

Conditions during the test are presented in Table 5.

TABLE 5

Conditions During Test

| Conditions during tests | Mean +/− Standard deviation |
|---|---|
| Lice transported in isolated box | T = 29.6 +/− 1.0° C.; RH = 30.1 +/− 3.0% |
| Room conditions during tests | T = 22.9 +/− 0.1° C.; RH = 28.8 +/− 0.5% |
| Water temperature during incubations | T = 32.0 +/− 0.3° C. |
| Heating plate during observations mortality | T = 37.0 +/− 0.5° C. |
| Storage of lice before/after treatment (test) | T = 31.8 +/− 0.1° C.; RH = 76.0 +/− 1.5% |
| Storage of lice before/after treatment (control) | T = 31.9 +/− 0.1° C.; RH = 76.8 +/− 1.3% |

Results and Conclusion

The following categories were used to describe the observations of louse eggs after completion of hatching to determine the effect of the treatment on the eggs and the developing embryos.

Hatched: Eggs (nits) that complete their development and nymph has emerged completely from the eggshell leaving a clear open shell.

Half-Hatched (Emergent): In some cases, the nymph developed fully but failed to completely emerge, since the nymph died in the process of escaping from the shell such that part of the nymph body remained in the eggshell.

Dead (Late): In some eggs, the embryo appeared to develop more or less fully but then died before lifting the cap of the shell as part of the hatching process. Typically, the eye spots were visible.

Undeveloped (Early): The newly laid egg had a more or less clear amorphous content, which only began to show the presence of the developing embryo after about 2-3 days from which point the dark eye spot of the insect appeared at the distal end of the eggshell. Failure to achieve this stage of development indicates death at an early point soon after exposure to the treatment.

The results shown in Table 6 below surprisingly demonstrate that the two exemplary compositions of the present application, F1 and F2 were 100% effective at killing louse eggs. All of the louse eggs, irrespective of the stage, were killed following treatment with F1 and F2 meaning 0 eggs hatched. The comparator product (Rcomparator) produced less effective results with 78.8% efficacy against the louse eggs. The negative control replicates behaved as expected with a very low level of mortality at 8.8%.

independent contract laboratory using rabbits as the source of maintenance feeding as per the ASTM E1517 13 test method.

Test Method

The eggs were tested according to the test method: ASTM E1517 13 method: Standard Test Method for Determining the Effectiveness of Liquid, Gel, Cream, or Shampoo Insecticides Against Human Louse Ova. The number of replicates was 5. All other methodology in the ASTM E1517 13 method was followed accordingly.

In summary, five replicates of 30 louse eggs were immersed in the test compositions for the incubation time indicated below. The louse eggs were then washed, rinsed with water and blotted dry, and incubated in separate petri dishes. For the negative control, the eggs were processed as with the eggs treated with the test compositions but immersed in water. When all the control eggs hatched (approximately 12 days), all replicates were examined to determine the state of the eggs.

Test Products

F2, 5 replicates, incubation time=10 minutes at 32° C.

F3, 5 replicates, incubation time=10 minutes at 32° C.

TABLE 6

Observed Effect of Compositions F1 and F2, and RComparator Against Louse Eggs

| Test Product | Replicate | Total | Hatched | Half Hatched (Emergent) | Dead (Late) | Undeveloped (Early) | % Mortality |
|---|---|---|---|---|---|---|---|
| Rcomparator | 1 | 30 | 9 | 0 | 12 | 9 | |
| | 2 | 30 | 2 | 0 | 24 | 4 | |
| | 3 | 30 | 8 | 0 | 15 | 7 | |
| | Total | 90 | 19 | 0 | 51 | 20 | 78.8% |
| F1 | 1 | 30 | 0 | 0 | 0 | 30 | |
| | 2 | 30 | 0 | 0 | 0 | 30 | |
| | 3 | 30 | 0 | 0 | 0 | 30 | |
| | Total | 90 | 0 | 0 | 0 | 90 | 100% |
| F2 | 1 | 30 | 0 | 0 | 0 | 30 | |
| | 2 | 30 | 0 | 0 | 0 | 30 | |
| | 3 | 30 | 0 | 0 | 0 | 30 | 100% |
| | Total | 90 | 0 | 0 | 0 | 90 | |
| Control | 1 | 30 | 29 | 0 | 1 | 0 | |
| | 2 | 30 | 28 | 0 | 1 | 1 | |
| | 3 | 30 | 25 | 0 | 1 | 4 | |
| | Total | 90 | 82 | 0 | 3 | 5 | 8.8% |

Example 3 Activity Against Louse Eggs

Exemplary compositions F2 and F3 of the present application were prepared using the general method as described in Example 1.

The activity of the exemplary compositions F2 and F3 against louse eggs was assessed using ASTM test method E1517 13 (Standard Test Method for Determining Effectiveness of Liquid, Gel, Cream, or Shampoo Insecticide Against Human Louse Ova). RComparator as defined in Example 2 was used as the comparator. Water was used as a negative control. A composition containing 49.8% isopropyl myristate, 49.8% cyclomethicone and 0.2% each of two common insecticides (ivermectin and methoprene) was used as a positive control.

Insects Used in the Tests

Body louse eggs, *Pediculus humanus humanus*, were obtained from the laboratory culture maintained by an RComparator, 5 replicates, incubation time=10 minutes at 32° C.

Positive Control, 5 replicates, incubation time=10 minutes at 32° C.

Negative control, water, 7 replicates, incubation time=10 minutes at 32° C.

Conditions during the test are presented in Table 7.

TABLE 7

Conditions During Test

| Conditions during tests | Mean +/− Standard deviation |
|---|---|
| Water temperature during incubations | T = 31.9 +/− 0.4° C. |
| Storage of lice before/after treatment (test) | T = 31.9 +/− 0.1° C.; RH = 76.9 +/− 1.3% |
| Storage of lice before/after treatment (control) | T = 32.1 +/− 0.0° C.; RH = 75.4 +/− 0.8% |

Results and Conclusion

The following categories were used to describe the observations of louse eggs after completion of hatching to determine the effect of the treatment on the eggs and the developing embryos.

Hatched: Eggs (nits) that complete their development and nymph has emerged completely from the eggshell leaving a clear open shell.

Half-Hatched (Emergent): In some cases, the nymph developed fully but failed to completely emerge, since the nymph died in the process of escaping from the shell such that part of the nymph body remained in the eggshell.

Dead (Late): In some eggs, the embryo appeared to develop more or less fully but then died before lifting the cap of the shell as part of the hatching process. Typically, the eye spots were visible.

Undeveloped (Early): The newly laid egg had a more or less clear amorphous content, which only began to show the presence of the developing embryo after about 2-3 days from which point the dark eye spot of the insect appeared at the distal end of the eggshell. Failure to achieve this stage of development indicates death at an early point soon after exposure to the treatment.

The results shown in Table 8 below surprisingly demonstrate that the two exemplary compositions of the present application, F2 and F3 were 100% effective at killing louse eggs. All of the louse eggs, irrespective of the stage, were killed following treatment with F2 and F3, meaning 0 eggs hatched. The comparator product (RComparator) produced less effective results with 78.4% efficacy against the louse eggs. Also less effective are the compositions of EP Patent No. 1993363 which were only demonstrated to kill louse eggs (Nits II) at 39.5% and 67.5% for Inv 1 and Inv 2, respectively. The negative control behaved as expected with a low level of mortality of 13.5%. The positive control was 98.7% effective at killing the louse eggs. A high kill rate was expected with the positive control given the presence of the common pesticides ivermectin and Methoprene.

TABLE 8

Observed Effect of Compositions F2 and F3, and RComparator and Positive/Negative Controls Against Louse Eggs

| Test product | Replicate | Total | Hatched | Half Hatched (Emergent) | Dead (Late) | Undeveloped (Early) | % Mortality |
|---|---|---|---|---|---|---|---|
| F2 | 1 | 30 | 0 | 0 | 0 | 30 | |
|  | 2 | 30 | 0 | 0 | 10 | 20 | |
|  | 3 | 30 | 0 | 0 | 0 | 30 | |
|  | 4 | 30 | 0 | 0 | 19 | 11 | |
|  | 5 | 30 | 0 | 0 | 0 | 30 | |
|  | Total | 150 | 0 | 0 | 29 | 121 | 100 |
| F3 | 1 | 30 | 0 | 0 | 0 | 30 | |
|  | 2 | 30 | 0 | 0 | 8 | 22 | |
|  | 3 | 30 | 0 | 0 | 0 | 30 | |
|  | 4 | 30 | 0 | 0 | 6 | 24 | |
|  | 5 | 30 | 0 | 0 | 0 | 30 | |
|  | Total | 150 | 0 | 0 | 14 | 136 | 100 |
| RComparator | 1 | 28 | 3 | 0 | 2 | 23 | |
|  | 2 | 30 | 5 | 1 | 11 | 13 | |
|  | 3 | 30 | 11 | 2 | 5 | 12 | |
|  | 4 | 30 | 9 | 0 | 8 | 13 | |
|  | 5 | 30 | 4 | 1 | 1 | 24 | |
|  | Total | 148 | 32 | 4 | 27 | 85 | 78.4 |
| Positive Control | 1 | 30 | 0 | 0 | 28 | 2 | |
|  | 2 | 30 | 0 | 0 | 7 | 23 | |
|  | 3 | 30 | 0 | 2 | 18 | 10 | |
|  | 4 | 30 | 0 | 0 | 14 | 16 | |
|  | 5 | 30 | 2 | 0 | 13 | 15 | |
|  | Total | 150 | 2 | 2 | 80 | 66 | 98.7 |
| Negative control | 1 | 28 | 23 | 0 | 2 | 3 | |
|  | 2 | 30 | 30 | 0 | 0 | 0 | |
|  | 3 | 30 | 21 | 1 | 7 | 1 | |
|  | 4 | 30 | 29 | 0 | 0 | 1 | |
|  | 5 | 30 | 27 | 1 | 2 | 0 | |
|  | 6 | 30 | 28 | 0 | 1 | 1 | |
|  | 7 | 30 | 22 | 2 | 6 | 0 | |
|  | Total | 208 | 180 | 4 | 18 | 6 | 13.5 |

Example 4 Activity Against Lice

Formulations F2 and F3 as described in Example 3 were assessed for direct kill of lice according to ASTM E938 Method Appendix 1 section 6. The comparator formulation RComparator was tested as well. Water was used as negative control.

Insects Used in the Tests

Body lice, *Pediculus humanus humanus*, were obtained from the laboratory culture maintained by an independent contract laboratory using artificially reared lice, a deviation from the ASTM E938 method Appendix 1 section 6, see File Note 1. Lice used in the tests were all adult lice.

Test Method

The lice were tested according to the test method: ASTM E938 method: Effectiveness of a Liquid, Gel, Cream, or Shampoo Insecticides against adult human lice.

Test Products:
F2: 5 replicates, incubation time=10 minutes at 32° C.
F3: 5 replicates, incubation time=10 minutes at 32° C.
RComparator: 5 replicates, incubation time=10 minutes at 32° C.
Negative control, water, 5 replicates, incubation time=10 minutes at 32° C.

Conditions during the test are presented in Table 9.

TABLE 9

Conditions During Test

| Conditions during tests | Mean +/− Standard deviation |
|---|---|
| Room conditions during tests | T = 21.7 +/− 0.2° C.; RH = 31.7 +/− 1.2% |
| Water temperature during incubations | T = 31.9 +/− 0.2° C. |
| Heating plate during observations mortality | T = 37.6 +/− 1.0° C. |
| Storage of lice before/after treatment (test) | T = 31.5 +/− 0.3° C.; RH = 76.3 +/− 0.5% |
| Storage of lice before/after treatment (control) | T = 31.6 +/− 0.0° C.; RH = 75.0 +/− 0.6% |

Results and Conclusion

To clarify the terms used in the evaluation tables it is necessary to classify the different categories of response obtained using the treatments:

"Immobile" describes lice that were completely immobile at the time the results were scored. Lice from this state may be considered to have died but could be immobilised by some stunning effect so mortality cannot be confirmed unless the insects fail to recover over a long period.

"Morbid" describes lice that retained some movement at the time the results were scored. Such movements can range from complete physical immobility, with just small movements of the gut observable; through minor twitches of limbs, antennae or other appendages; to insects that are nearly able to crawl but are sufficiently lacking in coordination that they could not be considered as capable of continued survival. Lice in this category are also classified in the overall mortality during the early stages of evaluation as being no longer effectively alive. In a final analysis, lice continuing to show signs of movement cannot be reliably considered to have died because, if they had been subjected to natural warmth and humidity on the scalp and provided with the opportunity to feed, a partial recovery could result in a full recovery.

"Alive" describes lice that appear to walk normally and would be expected, given the opportunity to feed, to be able to continue life in a normal manner.

All lice were observed to be completely immobile immediately after treatment and washing off. However, this is normal for lice immersed in a fluid and it can take several minutes up to 2-3 hours for all lice to dry out sufficiently to demonstrate whether that immobilisation effect is a true physiological knockdown or simply a wetting effect, especially when oily fluids are applied that may not be washed off easily by the rinsing process or that may evaporate slowly. The results of test readings at 1 hour and overnight are shown in separate tables below.

The observation 1 hour after testing (Table 10) showed that all the lice in all groups except the Control group remained immobile. There was no recovery from the knockdown effect of any of the treatments during this timepoint.

The final, overnight observation at approximately 24 hours post-treatment (Table 11) found no surviving lice in any of the test groups treated for 10 minutes.

Overall the results indicate there is complete activity of all the test formulations, F2, F3 and RComparator against adult body lice giving 100% efficacy with a 10 minute exposure and a water wash off.

TABLE 10

Observed effect of F2, F3 and RComparator against body lice at 1 hour post treatment

| Test Product | Replicate | Total | Alive | Morbid | Immobile | % Immobility |
|---|---|---|---|---|---|---|
| F2 | 1 | 25 | 0 | 0 | 25 | |
|  | 2 | 24 | 0 | 0 | 24 | |
|  | 3 | 25 | 0 | 0 | 25 | |
|  | 4 | 26 | 0 | 0 | 26 | |
|  | 5 | 26 | 0 | 1 | 25 | |
|  | Total | 126 | 0 | 1 | 125 | 100 |
| F3 | 1 | 26 | 0 | 0 | 26 | |
|  | 2 | 25 | 0 | 0 | 25 | |
|  | 3 | 25 | 0 | 0 | 25 | |
|  | 4 | 25 | 0 | 0 | 25 | |
|  | 5 | 25 | 0 | 4 | 21 | |
|  | Total | 126 | 0 | 4 | 122 | 100 |
| RComparator | 1 | 26 | 0 | 0 | 26 | |
|  | 2 | 25 | 0 | 0 | 25 | |
|  | 3 | 25 | 0 | 0 | 25 | |
|  | 4 | 25 | 0 | 2 | 23 | |
|  | 5 | 25 | 0 | 0 | 25 | |
|  | Total | 126 | 0 | 0 | 124 | 100 |
| Control | 1 | 26 | 26 | 0 | 0 | |
|  | 2 | 25 | 25 | 0 | 0 | |
|  | 3 | 25 | 25 | 0 | 0 | |
|  | 4 | 25 | 25 | 0 | 0 | |
|  | 5 | 25 | 25 | 0 | 0 | |
|  | Total | 126 | 126 | 0 | 0 | 0 |

TABLE 11

Observed effect of F2, F3 and RComparator against body lice at 24 hours post treatment

| Test Product | Replicate | Total | Alive | Morbid | Immobile | % Immobility |
|---|---|---|---|---|---|---|
| F2 | 1 | 25 | 0 | 0 | 25 | |
|  | 2 | 24 | 0 | 0 | 24 | |
|  | 3 | 25 | 0 | 0 | 25 | |
|  | 4 | 26 | 0 | 0 | 26 | |
|  | 5 | 26 | 0 | 0 | 26 | |
|  | Total | 126 | 0 | 0 | 126 | 100 |
| F3 | 1 | 26 | 0 | 0 | 26 | |
|  | 2 | 25 | 0 | 0 | 25 | |
|  | 3 | 25 | 0 | 0 | 25 | |
|  | 4 | 25 | 0 | 0 | 25 | |
|  | 5 | 25 | 0 | 0 | 25 | |
|  | Total | 126 | 0 | 0 | 126 | 100 |
| RComparator | 1 | 26 | 0 | 0 | 26 | |
|  | 2 | 25 | 0 | 0 | 25 | |
|  | 3 | 25 | 0 | 0 | 25 | |
|  | 4 | 25 | 0 | 0 | 25 | |
|  | 5 | 25 | 0 | 0 | 25 | |
|  | Total | 126 | 0 | 0 | 126 | 100 |

TABLE 11-continued

Observed effect of F2, F3 and RComparator against body lice at 24 hours post treatment

| Test Product | Replicate | Total | Alive | Morbid | Immobile | % Immobility |
|---|---|---|---|---|---|---|
| Control | 1 | 26 | 20 | 1 | 5 | |
| | 2 | 25 | 25 | 0 | 0 | |
| | 3 | 25 | 23 | 2 | 0 | |
| | 4 | 25 | 22 | 1 | 2 | |
| | 5 | 25 | 21 | 1 | 3 | |
| | Total | 126 | 111 | 5 | 10 | 11.9 |

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

The invention claimed is:

1. A composition comprising:
   a. one or more fatty acid esters; and
   b. one or more linear polymeric siloxanes,
   wherein the one or more linear polymeric siloxanes have a viscosity at 25° C. of greater than 2 cST to less than 89 cST, wherein the ratio of the one or more fatty acid esters to the one or more linear polymeric siloxanes is about 2:1 to about 1:2 and the composition is pourable or sprayable.

2. The composition of claim 1, wherein the one or more fatty acid esters are present in an amount of greater than 10 wt % by total weight of the composition.

3. The composition of claim 1, wherein the one or more linear polymeric siloxanes are present in an amount of less than 65 wt % by total weight of the composition.

4. The composition of claim 1, wherein the composition comprises one linear polymeric siloxane.

5. The composition of claim 1, wherein the composition is free of pesticides, or alternatively, further comprises a pesticide selected from the group consisting of piperonyl butoxide, permethrin, ivermectin, malathion, spinosad, lidane, methoprene, and combinations thereof.

6. The composition of claim 1, wherein the composition kills greater than 79%, of ectoparasite ova in about 24 hr following about 5 to about 10 minutes of topical contact of the composition with a subject.

7. The composition of claim 1, wherein the one or more fatty acid esters are selected from alkyl esters of fatty acids.

8. The composition of claim 1, wherein the one or more fatty acid esters are selected from myristate, laurate, palmitate, stearate, arachidate, behenate, lignocerate, palmitoleate, oleate, linoleate, linolenate, and arachidonate.

9. The composition of claim 8, wherein, the alkyl esters are selected from isopropyl esters, methyl esters, ethyl esters, and propyl esters.

10. The composition of claim 1, wherein the composition comprises one fatty acid ester.

11. The composition of claim 10, wherein the one fatty acid ester is isopropyl myristate.

12. The composition of claim 1, wherein the one or more linear polymeric siloxanes are linear polydialkylsiloxanes.

13. The composition of claim 1, wherein the one or more linear polymeric siloxanes are polydimethylsiloxanes.

14. The composition of claim 1, wherein the one or more linear polymeric siloxanes have a viscosity at 25° C. of greater than about 10 cSt to less than 89 cSt.

15. The composition of claim 1, wherein the one or more linear polymeric siloxanes have an average molecular weight (MW) of about 900 g/mol to about 6200 g/mol.

16. The composition of claim 1, wherein the composition comprises one linear polymeric siloxane.

17. The composition of claim 1, wherein the composition comprises about 40 wt % to about 60 wt % of the one or more fatty acid esters and about 40 wt % to about 60 wt % of the one or more linear polymeric siloxanes, by total weight of the composition.

18. The composition of claim 1, wherein a weight ratio of the one or more fatty acid esters to the one or more linear polymeric siloxanes is about 1:1.

19. The composition of claim 1, further comprising excipients, diluents, carriers, cosmetic agents, foaming agents, fragrances agents, and/or skin care agents.

20. A kit comprising a. one or more compositions of claim 1, and optionally b. instructions for use.

21. A method for treating an ectoparasite infestation on a subject in need thereof comprising topically administering one or more compositions of claim 1 to the subject.

22. The method of claim 21, wherein the treating comprises killing the ectoparasites and/or ova of the ectoparasites causing the ectoparasite infestation.

23. The method of claim 22, wherein the treating comprises killing ova of the ectoparasites that are undeveloped ova, developed ova, half-hatched ova, or combinations thereof.

24. The method of claim 22, wherein the ectoparasite infestation is caused by ectoparasites selected from head lice, body lice, crab lice, mites, fleas and ticks, and ova and/or larvae thereof.

25. The method of claim 24, wherein the ectoparasites are head lice.

26. The method of claim 21, wherein the administering comprises contacting the one or more compositions with an area on the subject where the infestation is present.

27. The method of claim 26, wherein the area is the scalp, hair or fur of the subject.

28. The method of claim 26, wherein the contacting is for about 5 minutes to about 40 minutes or about 5 to about 10 minutes.

29. The method of claim 22, wherein the composition kills greater than 79% of ectoparasite ova in about 24 hr, following the contacting.

30. The method of claim 21, wherein the one or more compositions are administered as a one-time use.

* * * * *